United States Patent [19]

Meyers et al.

[11] 3,949,001

[45] Apr. 6, 1976

[54] PROCESS FOR PRODUCING ARYL α-HALOALKYL SULFONES

[75] Inventors: Cal Yale Meyers; Walter Sidney Matthews, III, both of Carbondale, Ill.; Ashok M. Malte, Poona, India

[73] Assignee: Southern Illinois University Foundation, Carbondale, Ill.

[22] Filed: Dec. 17, 1973

[21] Appl. No.: 425,294

Related U.S. Application Data

[62] Division of Ser. No. 98,094, Dec. 14, 1970, Pat. No. 3,830,862.

[52] U.S. Cl............................................. 260/607 A
[51] Int. Cl.$^2$....................................... C07C 149/06
[58] Field of Search................................ 260/607 A

[56] References Cited
UNITED STATES PATENTS
3,830,862    8/1974    Meyers et al.................... 260/607 A FOREIGN PATENTS OR APPLICATIONS
2,110,519    11/1971    Germany........................ 260/607 A
647,215    11/1948    United Kingdom............. 260/607 A OTHER PUBLICATIONS
Goering et al., J.A.C.S. Vol. 79 pp. 2502–2506.
J. Org. Chem. Vol. 33 pp. 43–47.

*Primary Examiner*—Lewis Gotts
*Assistant Examiner*—D. R. Phillips
*Attorney, Agent, or Firm*—Koenig, Senniger, Powers and Leavitt

[57]    ABSTRACT

A process for preparing alkenes by reaction of various sulfone substrates with carbon tetrahalide in the presence of a strong base. The reactions are accelerated by the presence of a polar compound. Sulfone carbanions attack the carbon tetrahalide to produce an α-halogenated intermediate and a dihalocarbene. α-Halosulfones having α' hydrogens are converted to alkenes in situ via the Ramberg-Backland reaction. Sulfones having α but no α' hydrogens are simply α-halogenated. The dihalocarbene generated in the reaction may attack the product, solvent, or another substrate to form other products. Alkenes produced by reaction of carbon tetrahalides with di-sec-alkyl sulfones are readily attacked by dihalocarbene to form the alkene-dihalocarbene adduct (a substituted 1,1-dihalocyclopropane).

7 Claims, No Drawings

PROCESS FOR PRODUCING ARYL ALPHA-HALOALKYL SULFONES

This is a division of application Ser. No. 98,094 filed Dec. 14, 1970, now U.S. Pat. No. 3,830,862.

BACKGROUND OF THE INVENTION

This invention relates to the field of organic chemistry and more particularly to ionic reactions of certain carbon tetrahalides with various organic compounds.

Carbon tetrachloride is generally considered to be a compound of limited chemical reactivity and has found application in a number of services which capitalize on its relative chemical inertness. Thus, for example, carbon tetrachloride is useful as a fire extinguishing agent, as a cleaning solvent and as a solvent for organic chemical reactions. For many years carbon tetrachloride found its principal application as a solvent, particularly for cleaning purposes. Recently, this market has been substantially closed off, however, due to government restrictions relating to the toxicity of carbon tetrachloride.

The use of carbon tetrachloride as a chemical intermediate has heretofore been restricted to a few specialized reactions. Commercial production of chloroform, for example, is carried out by reduction of carbon tetrachloride with iron and water. Compounds marketed under the trade designation "Freons" such as dichlorodifluoromethane and trichloromonofluoromethane are produced commercially by partially displacing chlorine from carbon tetrachloride with fluorine. The production of such "Freon" compounds has represented the principal commercial outlet for carbon tetrachloride for several years, and in recent years has provided the only major market for this material.

In 1876, Reimer and Tiemann discovered that phenol could be converted to ortho and parahydroxybenzaldehydes by reaction with chloroform in an aqueous alkaline medium. When they substituted carbon tetrachloride for chloroform, added ethanol and held the reaction mixture in a sealed tube at 100°C. for 3 days, a mixture of ortho and parahydroxy benzoic acid was produced. The work of Reimer and Tiemann with carbon tetrahalides was limited to the particular reaction noted above, i.e., the addition of a carboxylic acid group para or ortho to a phenolic hydroxy group, using an ethanolic aqueous alkaline medium.

Because of its abundance and relative inexpensiveness, carbon tetrachloride is potentially a very attractive chemical intermediate. Prior to the present invention, however, this compound was considered to be a substantially inert material whose chemical activity was limited to certain particular reactions such as those outlined above.

SUMMARY OF THE INVENTION

Among the several objects of the present invention, therefore, may be mentioned the provision of a method for producing useful compounds by reaction of various sulfone substrates with carbon tetrahalides such as carbon tetrachloride and carbon tetrabromide; the provision of a method whereby certain organic compounds can be produced in a more convenient and economical manner than has previously been practical; and the provision of a method for producing certain alkenes and their dihalocarbene adducts. Other objects and features will be in part apparent and in part pointed out hereinafter.

The present invention is thus directed to a process for preparing substituted alkenes which comprises the steps of reacting a substrate selected from the group consisting of substituted dibenzyl sulfones having $\alpha$ and $\alpha'$ hydrogens, unsubstituted dibenzyl sulfones having $\alpha$ and $\alpha'$ hydrogens, substituted di-sec-alkyl sulfones having $\alpha$ and $\alpha'$ hydrogens and unsubstituted di-sec-alkyl sulfones with a carbon tetrahalide represented by the formula $CBr_mCl_nF_p$ where m and n are integers between 0 and 4 inclusive, p is an integer between 0 and 2 inclusive, and $m+n+p=4$, in the presence of a strong base to form a halogenated intermediate and a dihalocarbene; and reacting said halogenated intermediate with the base to form an alkene. Alkenes derived from di-sec-sulfones can react with dihalocarbene to form substituted 1,1-dihalocyclopropanes. The invention is also directed to a process for preparing aryl $\alpha$-haloalkyl sulfones from aryl alkyl sulfones which comprises the steps of reacting an aryl alkyl sulfone with a carbon tetrahalide of the above-noted character in the presence of a strong base to form an $\alpha$-halogenated product and a dihalocarbene.

DESCRIPTION OF THE PREFERRED EMBODIMENTS

It has now been discovered that carbon tetrachloride and certain other carbon tetrahalides can be made to react with various sulfones to produce a number of useful products. In the presence of a strong base, normally unreactive carbon tetrahalides such as carbon tetrachloride and carbon tetrabromide react with a variety of sulfone substrates. Where the substrate has both $\alpha$ and $\alpha'$ hydrogens, as in dibenzyl sulfone and di-sec-alkyl sulfones, a carbon-carbon double bond is produced in place of the sulfonyl group. Sulfones having $\alpha$ but no $\alpha'$ hydrogens are $\alpha$-halogenated and certain of these halogenated species may undergo subsequent reaction to form other products. The reactions of this invention proceed rapidly at moderate temperatures, for example room temperature or less up to about 250°C., and produce a wide range of products in good yield, certain of which are impractical or uneconomical to produce according to previously known methods.

While we do not wish to be held to any particular theory, it is postulated that the reactions involved in the process of the present invention proceed according to the following equations (where $CCl_4$ is shown as an illustrative carbon tetrahalide and R is hydrogen or alkyl):

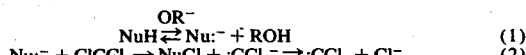
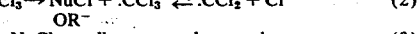
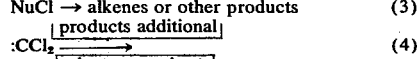

In reaction (1) the substrate material (NuH) associates with the strong base, yielding a nucleophilic anion Nu:⁻. The anion in turn attacks one of the halogen atoms of the carbon tetrahalide [equaton (2)], yielding a halogenated intermediate and a trihalomethyl anion which dissociates into a dihalocarbene and a halide ion. The halogenated intermediate may undergo further halogenation or react intramolecularly to form alkenes or other products as in equation (3). Depending upon the nature of the substrate, the dihalocarbene may react with the substrate products, solvent or another substrate to form additional products, as indicated in equation (4).

The halogenation step indicated in equation (2) takes place quite readily and once monohalogenation has taken place, multiple halogenation at that atom proceeds even more rapidly. Where the nature of the substrate allows intramolecular reaction of the monohalogenated species by means of the strong base, however, the latter reaction takes place much more rapidly than dihalogenation and alkenes are preferentially produced. Thus, a novel route is provided to various unsaturated compounds with the monohalogenation step indicated in equation (3) being the rate controlling step.

Under conditions wherein the strong base remains a solid during the reaction, the halide ion produced in equation (2) forms the halide salt of the metal of the strong base and precipitates. This halide salt often tends to collect at and coat the surface of the strong base, thus impeding the formation of the Nu:⁻ anion per equation (1) and the formation of products per equation (3). The rates and yields of the reactions of the invention, particularly those where the kinetics of the anion formation are relatively slow, may be adversely affected by this phenomenon. It is preferred, therefore, that a small quantity of water be present in the reaction medium, especially in those reactions where anion formation is slow. In such instances, the presence of an amount of water on the order of one mole per mole of substrate dissolves the halide salt as it is formed and prevents the interference of the salt with the formation of either the carbanion or the products.

The reactions of this invention are accelerated if a solvent for the substrate and the carbon tetrahalide is incorporated in the reaction system. A wide range of solvents, particularly polar solvents, may be utilized for this purpose. Thus, for example, an alcohol, polyol, cyclic ether, aliphatic ether, cyclic polyether, aliphatic polyether, tetrahydrofuran, glyme, diglyme, liquid ammonia or liquid sulfur dioxide serves as a suitable solvent. $t$-Butyl alcohol has been found to be a particularly useful polar solvent since it does not react with the substrate and has sufficient volatility to be readily stripped off during product recovery. Where the substrate is a substituted or unsubstituted dibenzyl sulfone, the presence of a polar compound such as water affords high reaction rates and yields.

The preferred carbon tetrahalide reactant is carbon tetrachloride. However, $CBr_4$ will also perform satisfactorily in these reactions, as will $CBrCl_3$, $CBr_2Cl_2$, $CBr_3Cl$, $CCl_3F$, $CCl_2BrF$, $CClBr_2F$, $CBr_3F$, $CCl_2F_2$, $CClBrF_2$ and $CBr_2F_2$. Generally, therefore, any compounds having the formula $CBr_mCl_nF_p$ where m and n are integers between 0 and 4 inclusive, p is an integer between 0 and 2 inclusive, and m+n+p = 4 can be utilized as the tetrahalide reactant in this invention.

The strong base used in this invention is preferably an alkaline hydroxide, e.g., NaOH or KOH, or a metal alkoxide such as a sodium, potassium or aluminum alkoxide.

In accordance with the reaction scheme of this invention, a strong base associates with sulfones having α-hydrogens and abstracts an α-hydrogen as a proton from an α-carbon. The resulting anion is then monohalogenated by the carbon tetrahalide. Where the substrate is a sulfone such as a dibenzyl sulfone, di-sec-alkyl sulfone, an α,α' disubstituted diprimary alkyl sulfone, or a secondary alkyl α-substituted primary alkyl sulfone, which possesses both α and α' hydrogens, the sulfone bridge is converted to a carboncarbon double bond via the Ramberg-Backland reaction. Thus, the mono-α-halo sulfone is converted to an episulfone, which is in turn converted in situ into an alkene by loss of $SO_2$. This reaction may be summarized by the chemical equations set forth below. Typically, the substrate may be

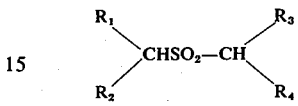

where at least one of $R_1$ and $R_2$ and at least one of $R_3$ and $R_4$ are substituted or unsubstituted aryl. The others of $R_1$, $R_2$, $R_3$ and $R_4$ are hydrogen, alkoxy, aryloxy, alkylthio, arylthio, nitro, cyano, amino, substituted amino or substituted or unsubstituted alkyl, aryl, aralkyl, alkynyl, alkenyl, aralkenyl, aralkynyl, cycloalkyl, or cycloalkenyl; or the substrate may be $A-SO_2-B$ where A and B are selected from the group consisting of sec-alkyl, aryl sec-alkyl, cycloalkyl and substituents having the general formula

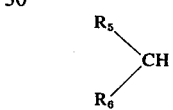

where $R_5$ and $R_6$ are selected from the group consisting of alkoxy, aryloxy, alkylthio, arylthio, nitro, cyano, amino, substituted amino and substituted or unsubstituted alkyl, aryl, aralkyl, alkenyl, aralkenyl, alkynyl, aralkynyl, cycloalkyl and cycloalkenyl. In either case the reaction proceeds as follows (where $CCl_4$ is shown as an illustrative tetrahalide) when

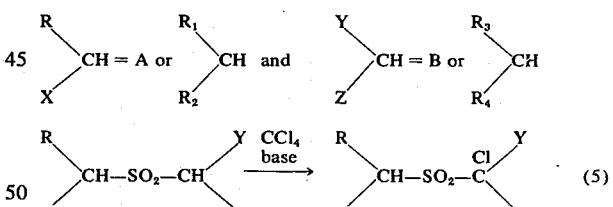

(5)

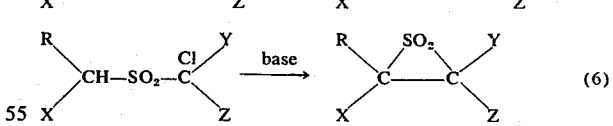

(6)

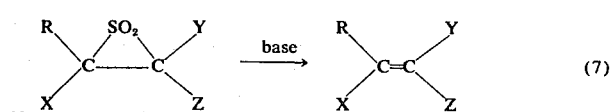

(7)

Essentially any substituted or unsubstituted dibenzyl sulfone having α and α' hydrogens is converted to its corresponding stilbene derivative and essentially any di-sec-alkyl sulfone having α and α' hydrogens is converted to its corresponding alkene in accordance with the processes of this invention. Illustrative dibenzyl sulfones and di-sec-alkyl sulfones which are so converted include:

dibenzyl sulfone
di-α-methylbenzyl sulfone
dl-α-methylbenzyl sulfone
meso-α-methylbenzyl sulfone
2-thia-2,3-dihydrophenalene 2,2-dioxide
di-sec-butyl sulfone
dicyclohexyl sulfone
dicyclopentyl sulfone
9-thiabicyclo[3.3.1]nonane 9,9-dioxide
di-isopropyl sulfone

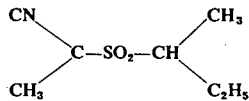

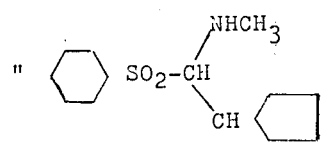

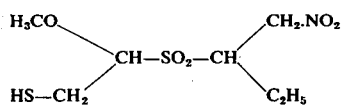

Not only does the reaction scheme of this invention provide a uniquely advantageous route to alkenes, but it also affords a route to specific geometric isomers. Thus, dibenzyl sulfone is converted to 100 percent trans-stilbene. Also dl-α-methylbenzyl sulfone is converted into 72 percent of the trans and 28 percent of the cis α,β-dimethylstilbene. When meso α-methylbenzyl sulfone is the substrate, on the other hand, a yield of 90 percent of the cis and only 10 percent trans α,β-dimethylstilbene are realized.

Where a di-sec-alkyl sulfone is employed as the substrate, the dihalocarbene generated by the attack of carbon tetrahalide on the sulfone can add across the alkene double bond to form a substituted 1,1-dihalocyclopropane. The latter compounds are often the major products of this reaction, suggesting that most of the dihalocarbene generated in the reaction of the sulfonyl carbanion with carbon tetrahalide reacts rapidly with the alkene formed.

Aryl alkyl sulfones having no α' hydrogens cannot undergo the Ramberg-Backland reaction and are simply α-halogenated. Where the substrate has two or three hydrogens, di- and trihalogenation proceed at successively more rapid rates. Thus, quantitative halogen substitution of the α hydrogens always takes place with such substrates. The trihalomethyl sulfones resulting from the reactions of carbon tetrahalide with aryl α-methyl sulfones are highly subject to nucleophilic cleavage under the alkaline conditions of the reaction system and are quite easily broken down to aryl sulfonic acids.

The reactions of this invention proceed rapidly in high yield at moderate temperatures. Temperatures from just above the solidification point of the reaction system up to a temperature of about 250°C. may be employed. Higher temperatures can be tolerated but are normally unnecessary. Conveniently the reactions are simply carried out at room temperature. To facilitate particularly rapid reactions and high conversion, the reaction system is maintained above atmospheric reflux temperature, for example 150°C.

The relative proportions of reactants are in no way critical, and may be varied widely. A substantial excess of carbon tetrahalide, base and polar solvent promotes rapid reaction and high conversions. Lower excesses, however, provide larger reactor payloads and, as will be appreciated by those skilled in the art, the optimum commercial reactant ratios depend on the substrates and products involved, the capacities desired, the separation processes selected, and whether batch or continuous operations are employed.

In the processes of this invention, the product is recovered from the reaction mixture by any convenient means known to the art. One such method simply involves addition of water and an organic solvent to the reaction mixture, separation of the resulting aqueous phase from the organic phase, and recovery of the product from the organic phase as by stripping of the solvent therefrom.

As a result of the high rates and yields realized under mild conditions, and the low cost of reagents such as carbon tetrachloride, the reactions of this invention possess unique advantages over previously known methods of producing stilbenes and other olefins and 1,1-dihalocyclopropanes. Particular advantages accrue from the capability of producing geometrically specific olefins, as noted above.

The following examples illustrate the invention.

EXAMPLE 1

0.137 g. of meso-α-methylbenzyl sulfone and 0.4 g. of powdered potassium hydroxide were stirred in 10 ml. of carbon tetrachloride and 10 ml. of tertiary butyl alcohol under reflux (80°–82°C.) for 45 minutes. Excess solvent was removed under vacuum, a small proportion of water was added, and the residue was extracted with ether. The ether extract was then washed with water, dried with anhydrous magnesium sulfate, filtered and concentrated under vacuum to give 0.097 g. of product. The components of the product were separated by crystallization from aqueous methanol, and the product was found to consist of 90 percent by weight of cis-α,β-dimethyl stilbene and 10 percent by weight of trans-α,β-dimethyl stilbene.

EXAMPLE 2

0.137 g. of dl-α-methylbenzyl sulfone and 0.4 g. of powdered potassium hydroxide were stirred in 10 ml. of carbon tetrachloride and 10 ml. of tertiary butyl alcohol under reflux for 45 minutes. Excess solvent was removed under vacuum and a small proportion of water was added to the residue, which was then extracted with ether. The ether extract was washed with water, dried with anhydrous magnesium sulfate, filtered and concentrated under vacuum to give 0.10 g. of product. The components of the product were separated by crystallization from aqueous methanol and the product was found to consist of about 28 percent by weight of cis-α,β-dimethyl stilbene and 72 percent by weight trans-α,β-dimethyl stilbene.

EXAMPLE 3

1.16 g. phenyl benzyl sulfone and 5.6 g. of powdered potassium hydroxide were stirred in 10 ml. of carbon tetrachloride and 10 ml. of tertiary butyl alcohol under reflux for 30 minutes. Excess solvent was removed under vacuum, a small proportion of water was added to the residue, and the residue was extracted with ether. The ether extract was washed with water, dried with anhydrous magnesium sulfate, filtered and concentrated under a vacuum, yielding 1.5 g. of $\alpha,\alpha$-dichlorobenzyl phenyl sulfone.

EXAMPLE 4

2.1 g. of cyclopentyl phenyl sulfone (m.p. 60.1°–61.5°C.) were dissolved in 5 ml. of tertiary butyl alcohol and 15 ml. of carbon tetrachloride. 8 g. of powdered potassium hydroxide were added and the solution was refluxed for 20 minutes. The resultant salts and excess potassium hydroxide were filtered off, and the solvent was removed under vacuum. The residue was crystallized from benzene, yielding 2.36 g. of $\alpha$-chlorocyclopentylphenyl sulfone, m.p. 112°–113°C. Analysis by ir and nmr spectra and elemental analysis (C,H,S,Cl) were consistent with the structure. This is a novel compound which would appear to possess pesticidal properties.

The cyclopentyl phenyl sulfone used in this synthesis is also a novel compound. It was initially prepared by reacting benzenethiol with cyclopentyl bromide to form cyclopentyl phenyl sulfide which was in turn oxidized to produce the sulfone. Benzenethiol was reacted with cyclopentyl bromide in the presence of potassium carbonate in an acetone solvent at reflux temperature for 4 hours. The acetone was stripped off, water added, and 30–60 petroleum ether used to extract the sulfide. The ether phase was washed twice with 5 percent sodium hydroxide, once with water, and dried with anhydrous magnesium sulfate. The petroleum ether was then distilled off, leaving a residue which was used in the preparation of the sulfone.

A 2 mole excess of 30 percent hydrogen peroxide in a glacial acetic acid solvent was added to the residue containing the sulfide. The resulting mixture was kept at 70°C. for 1 hour, then refluxed for another hour. Most of the acetic acid was then stripped off under vacuum and the remaining solution added to a cold 5 percent sodium hydroxide solution. The sulfone product was extracted from the latter solution with ether, and the resulting ether phase was dried with anhydrous magnesium sulfate and then distilled to strip off the ether solvent. The residue was recrystallized from 60–90 ligroin to give a white crystalline solid having a melting point of 60.5°–61.5°C. and identified as cyclopentyl phenyl sulfone by ir, nmr and elemental analysis.

EXAMPLE 5

2.36 g. of dibenzyl sulfone were dissolved in 5 ml. of tertiary butyl alcohol and 15 ml. of carbon tetrachloride. 8 g. of powdered potassium hydroxide were added, and the resulting mixture was refluxed for 20 minutes. The solvent was removed under vacuum, and a small proportion of water added to the residue. The resultant alkaline aqueous solution was extracted twice with ether. The ether extract was dried with anhydrous magnesium sulfate and the ether solvent stripped off under vacuum, yielding 1.70 g. of trans-stilbene.

EXAMPLE 6

2.3 g. of dicyclohexyl sulfone were dissolved in 5 ml. of tertiary butyl alcohol and 15 ml. of carbon tetrachloride. 8 g. of powdered potassium hydroxide were added, and the resulting mixture was refluxed for 20 minutes. The solvent was then removed under vacuum and a small proportion of water added to the residue. The resulting aqueous alkaline phase was extracted twice with ether. The ether extract was dried with anhydrous magnesium sulfate, and the ether solvent removed under vacuum, yielding a yellow sweet-smelling solid, 2.03 g., having a melting range of 30°–46°C. The solid thus recovered was dissolved in a hot solvent consisting of 75 percent acetone and 25 percent water, and the resulting solution cooled to 0°C. 1.48 g. of a white solid precipitated, identified as 2,3-dicyclohexyl-1,1-dichloropropane, m.p. 83.5°–85°C., whose structure was confirmed by nmr and ir spectral analysis and elemental analysis (C,H,S,Cl). The mother liquor was concentrated in vacuo and yielded 0.55 g. of an oil which was purified by sublimation into a solid, m.p. 52°–54°C. and characterized as cyclohexylidene cyclohexane, whose properties compared favorably with those previously reported for this compound.

EXAMPLE 7

1 g. of 9-thiabicyclo[3.3.1]nonane 9,9-dioxide was dissolved in 2 ml. of tertiary butyl alcohol and 10ml. of carbon tetrachloride. 4 g. of powdered potassium hydroxide were added and the mixture was refluxed for 15 minutes and then cooled. A small proportion of water was added and the insoluble material that formed (0.5 g.) was removed by filtration and characterized as starting material. The organic phase of the mother liquor was isolated and stripped of solvent, giving 0.4 g. of a sweet-smelling oil. About 2 ml. of a mixture of 75 percent acetone in water was added to the oil and this solution was cooled to −10°C. The solid that separated was removed by filtration, yielding 0.24 g., m.p. 40°–41°C. which increased to 40.5°–41.5°C. when the solid was purified by sublimation. This material was characterized as 9,9-dichlorotricyclo(3.3.1.0)-nonane by nmr and ir spectral analysis and elemental analysis (C, H, Cl). The mother liquor was concentrated carefully in vacuo at low temperatures to yield an oil, 0.20 g., which contained mainly Δ1,5-bicyclooctene, a known compound whose properties have been previously reported.

EXAMPLE 8

2.46 g. of phenyl $\alpha$-methylbenzyl sulfone were dissolved in 5 ml. of tertiary butyl alcohol and 10 ml. of carbon tetrachloride. 8 g. of powdered potassium hydroxide were added and the resulting mixture was stirred at room temperature for 3 hours. The salts which formed were filtered off along with the excess potassium hydroxide, and the solvent was stripped off under vacuum. The residue was recrystallized from benzene, yielding 2.8 g. of an off-yellow solid characterized as phenyl $\alpha$-chloro-$\alpha$-methylbenzyl sulfone, m.p. 134°–135°C. by nmr and ir spectra and elemental analysis (C, H, S, Cl).

EXAMPLE 9

A mixture of 0.2388 g. of 2-thia-2,3-dihydrophenalene 2,2-dioxide, 2.4528 g. of powdered potassium hydroxide, 0.2 ml. of water and 5 ml. of carbon tetrachloride was stirred under reflux for 5 hours. The reaction mass was cooled and a small proportion of water added thereto. The resulting mixture was extracted with petroleum ether and the extract washed with dilute potassium hydroxide, dried with anhydrous magnesium sulfate, filtered and concentrated under vacuum, yielding 0.0721 g. of acenaphthylene.

EXAMPLE 10

0.01 Mole of diisopropyl sulfone was dissolved in 5 ml. of tertiary butyl alcohol and 15 ml. of carbon tetrachloride. 8 g. of powdered potassium hydroxide were added, and the resulting mixture was refluxed for 20 minutes. The solvent was then removed under vacuum and a small proportion of water added to the residue. The resulting aqueous alkaline phase was extracted twice with ether. The ether extract was dried with anhydrous magnesium sulfate, and the ether solvent removed under vacuum, yielding a yellow sweet-smelling solid, 2.03 g., having a melting range of 30°–46°C. The solid thus recovered was dissolved in a hot solvent consisting of 75 percent acetone and 25 percent water, and the resulting solution cooled to 0°C. 1.48 g. of a white solid precipitated, identified as 30 percent 2,3-dimethyl-2-butene and 61 percent 1,1-dichloro-2,2,3,3-tetramethylcyclopropane, whose structure was confirmed by nmr and ir spectral analysis and elemental analysis (C, H, S, Cl).

What is claimed is:

1. A process for preparing aryl α-haloalkyl sulfones from aryl alkyl sulfones which comprises the steps of: reacting an aryl alkyl sulfone with a carbon tetrahalide represented by the formula $CBr_mCl_nF_p$ where m is an integer between 0 and 4 inclusive, p is an integer between 0 and 2 inclusive, and $m+n+p=4$, in the presence of a strong base to form an α-halogenated product and a dihalocarbene.

2. In a process as set forth in claim 1, a solvent for the substrate and the carbon tetrahalide also being present.

3. In a process as set forth in claim 1, the carbon tetrahalide being carbon tetrachloride.

4. In a process as set forth in claim 1, the strong base being selected from the group consisting of alkaline hydroxides and metal alkoxides.

5. In a process as set forth in claim 1, the initial reaction being carried out at a temperature between the solidification point of the reaction mixture and about 250°C.

6. In a process as set forth in claim 4, said strong base being potassium hydroxide.

7. In a process as set forth in claim 2, said solvent being t-butyl alcohol.

* * * * *